United States Patent [19]

Engh et al.

[11] Patent Number: 6,139,581
[45] Date of Patent: Oct. 31, 2000

[54] POSTERIOR COMPENSATION TIBIAL TRAY

[75] Inventors: Gerard A Engh, Alexandria, Va.; Deborah S German, Plymouth; Jeff R Webb, Warsaw, both of Ind.

[73] Assignee: Depuy Orthopaedics, Inc., Warsaw, Ind.

[21] Appl. No.: 08/871,398

[22] Filed: Jun. 6, 1997

[51] Int. Cl.⁷ .................................................. A61F 2/38
[52] U.S. Cl. .................................... 623/20.34; 623/20.28; 623/20.31
[58] Field of Search ................... 623/20.14–20.36, 623/18.11, 16.11

[56] References Cited

U.S. PATENT DOCUMENTS

| | | |
|---|---|---|
| D. 365,396 | 12/1995 | Hayes . |
| D. 369,863 | 5/1996 | Hayes . |
| D. 373,825 | 9/1996 | Hayes . |
| 3,837,009 | 9/1974 | Walker . |
| 3,964,106 | 6/1976 | Hutter, Jr. et al. . |
| 4,209,861 | 7/1980 | Walker et al. . |
| 4,213,209 | 7/1980 | Insall et al. . |
| 4,759,767 | 7/1988 | Lacey . |
| 4,769,039 | 9/1988 | Horber . |
| 4,808,185 | 2/1989 | Penenberg et al. . |
| 4,936,853 | 6/1990 | Fabian et al. ............................ 623/20 |
| 4,950,298 | 8/1990 | Gustilo et al. . |
| 4,963,152 | 10/1990 | Hofmann et al. ........................ 623/20 |
| 4,963,153 | 10/1990 | Noesberger et al. ..................... 623/20 |
| 5,019,103 | 5/1991 | Van Zile et al. . |
| 5,047,058 | 9/1991 | Roberts et al. . |
| 5,108,442 | 4/1992 | Smith ....................................... 623/20 |
| 5,137,536 | 8/1992 | Koshino . |
| 5,282,803 | 2/1994 | Lackey . |
| 5,290,313 | 3/1994 | Heldreth . |
| 5,356,414 | 10/1994 | Cohen et al. . |
| 5,358,530 | 10/1994 | Hodorek . |
| 5,370,693 | 12/1994 | Kelman et al. . |
| 5,387,241 | 2/1995 | Hayes . |
| 5,405,396 | 4/1995 | Heldreth et al. . |
| 5,458,637 | 10/1995 | Hayes ....................................... 623/20 |
| 5,507,820 | 4/1996 | Pappas . |
| 5,509,934 | 4/1996 | Cohen . |
| 5,514,140 | 5/1996 | Lackey . |
| 5,531,793 | 7/1996 | Kelman et al. . |
| 5,549,686 | 8/1996 | Johnson et al. . |
| 5,824,103 | 10/1998 | Williams ................................... 623/20 |
| 5,871,545 | 2/1999 | Goodfellow et al. ..................... 623/20 |

OTHER PUBLICATIONS

Smith & Nephew Richards, Inc., Brochure: Genesis® II Total Knee System—System Overview, Copyright 1996.
Zimmer, Inc., Brochure: NexGen®, The Complete Knee Solution.

*Primary Examiner*—V. Millin
*Assistant Examiner*—Tram A. Nguyen
*Attorney, Agent, or Firm*—Barnes & Thornburg

[57] ABSTRACT

An apparatus is provided for replacing at least a portion of a proximal tibia. The tibial tray apparatus includes a posterior compensation element configured for extension across a resected surface of the tibia and formed to include a proximal surface, a distal surface, and a side wall and a stem extending from and being unitary with the distal surface. The side wall of the posterior compensation element includes an anterior region with an anterior height and a posterior region with a posterior height, the posterior height being greater than the anterior height.

24 Claims, 7 Drawing Sheets

POSTERIOR COMPENSATION TIBIAL TRAY

BACKGROUND AND SUMMARY OF THE INVENTION

The present invention relates to a prosthetic tibial component, and particularly to a tibial tray component that compensates for bone removed from the posterior proximal tibia. More particularly, the present invention relates to a tibial tray component that has a cross-section that is configured for coupling to a proximal tibia resected to remove a greater amount of bone from the posterior end of the proximal tibia than from the anterior end of the proximal tibia.

Surgeons often replace damaged or diseased knees with conventional femoral and tibial components that cooperate to create a prosthetic articulating joint. See, for example, U.S. Pat. No. 4,759,767, entitled "Prosthesis for Tibial Component of Knee Joint," to James A. Lacey. These conventional tibial components often include a tibial tray that replaces the natural tibial plateau in the prosthetic joint. During traditional primary or revision surgery, good bone is often removed to accommodate the conventional prosthetic implant. It is desirable to minimize the removal of good tibial bone during surgery. In addition, surgeons replace diseased or damaged bone with augments or modular components shown in, for example U.S. Pat. No. 5,019,103, entitled "Tibial Wedge System," to Richard R. Van Zile et al., and U.S. Pat. No. 5,370,693, entitled "Orthopedic Implant Augmentation and Stabilization Device," to David C. Kelman et al., to "fill" the aperture left in the tibia following bone removal. What is needed is a tibial tray component that is suitable for use in both primary and revision surgery that minimizes the necessary amount of tibial bone removal.

According to the present invention, a tibial tray apparatus is provided. The tibial tray apparatus is suitable for replacing at least a portion of the proximal end of a tibia having an anterior end, a posterior end, and a resected surface extending between the anterior and posterior ends. The tibial tray apparatus includes a posterior compensation element that includes a proximal surface, an opposite distal surface configured for extension across the resected surface between the anterior and posterior sides, and a side wall extending between the proximal and distal surfaces. The side wall includes an anterior region having an anterior height and a posterior region having a posterior height. The posterior height of the posterior region is greater than the anterior height of the anterior region.

According to another embodiment of the present invention, a tibial tray apparatus suitable for replacing at least a portion of the proximal end of a tibia is provided. The tibial tray apparatus comprises a plateau element that includes a proximal surface, an opposite distal surface, and a side wall extending between the proximal and distal surfaces. The side wall has an anterior region with an anterior height and an opposite posterior region with a posterior height. The posterior height is greater than the anterior height. In addition, the tibial tray apparatus includes a stem that extends from the distal surface of the plateau element.

In yet another embodiment of the present invention, a prosthetic apparatus is provided that is suitable for replacing at least a portion of a tibia. The prosthetic apparatus comprises a tibial tray including a plateau having proximal and distal surfaces cooperating to define an anterior region with an anterior height and an opposite posterior region with a posterior height. The posterior height is greater than the anterior height. In addition, the prosthetic apparatus includes a stem that extends from the distal surface and is positioned to lie between the anterior region and the posterior region. Further, a stem extension is provided that includes an interior surface defining a stem-receiving cavity therein. The interior surface is configured for locking engagement with the stem of the tibial tray component.

In still another embodiment of the present invention, a method of replacing a proximal end of a tibia that includes a posterior end and an opposite anterior end is provided. The method comprises the steps of forming a resected surface of the proximal tibia to have a distal posterior slope and providing a generally wedge-shape plateau component having a proximal surface and an opposite distal surface. The distal surface diverges from the proximal surface by a downward posterior angle to form an anterior region with an anterior height and a posterior region with a posterior height that is greater than the anterior height. In addition, the method further includes the step of positioning the distal surface of the plateau on the resected surface so that posterior region of the plateau is adjacent the posterior end.

Additional features of the present invention will become apparent to those skilled in the art upon consideration of the following detailed description of preferred embodiments exemplifying the best mode of carrying out the invention as presently perceived.

DETAILED DESCRIPTION OF THE DRAWINGS

Figure 1:
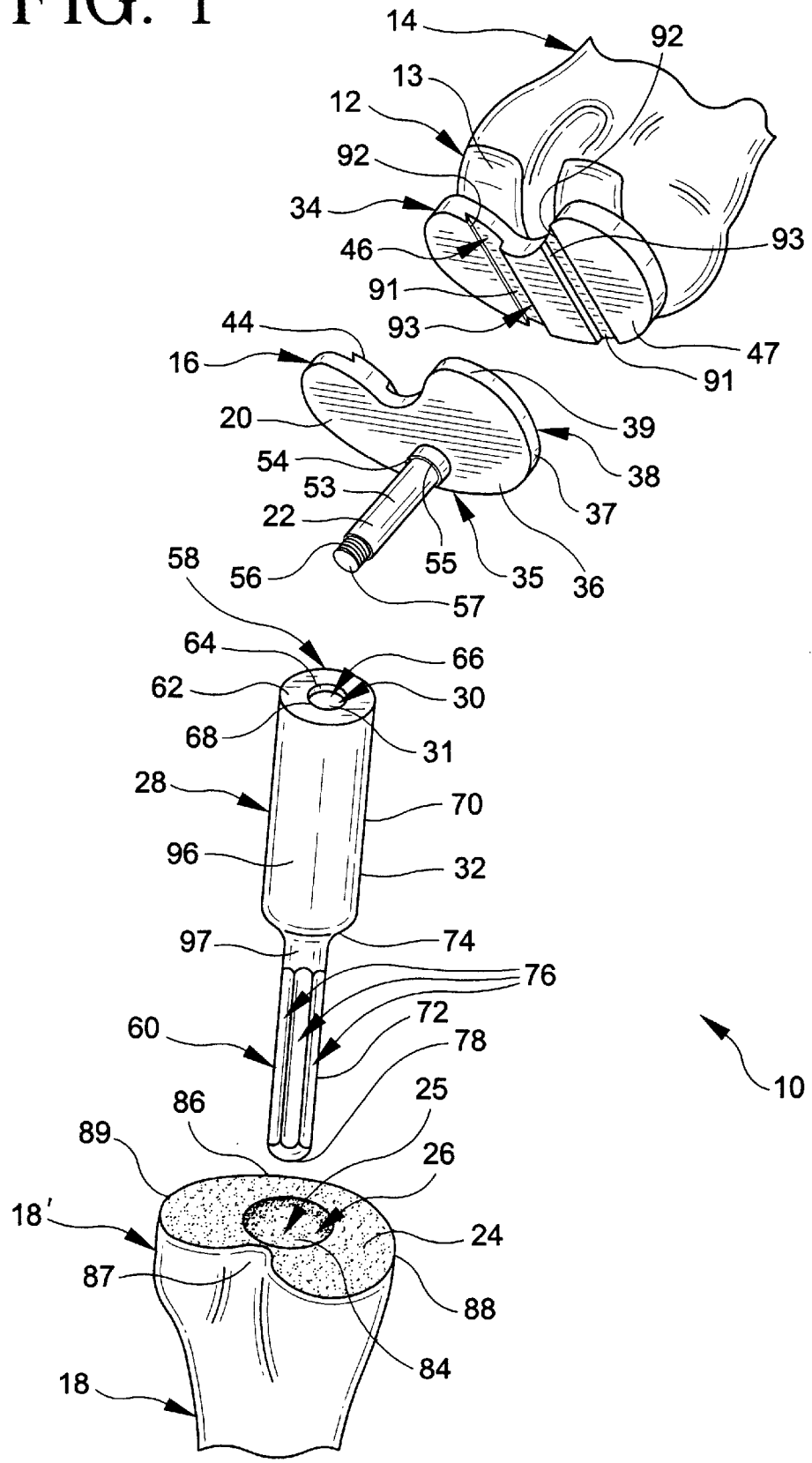
FIG. 1 is an exploded perspective view of a prosthetic knee prior to assembly showing a tibial tray component of the present invention having a stem and a generally wedge-shaped plateau element including dovetails thereon, a corresponding prosthetic femoral component, and a stem extension.

A tibial tray component 10 in accordance with the present invention is shown in FIG. 1 as it would appear just prior to assembly of a prosthetic knee 11. The tibial tray component 10 is suitable for use with prosthetic knees 11 that include a femoral component 12 and a stem extension 28. Once assembled, the tibial tray component 10 cooperates with the femoral component 12 and stem extension 28 to form the prosthetic knee 11. The tibial tray component 10 is configured to minimize the necessary amount of tibial bone removal in both primary and revision knee replacement. In preferred embodiments, tibial tray component 10 and stem extension 28 are formed from surgical grade stainless steel, although the invention contemplates use of any material with appropriate structural characteristics, such as titanium, cobalt, composite materials, etc.

The tibial tray component 10 is suitable for use with a tibia 18. The tibia 18 includes a proximal end 18', a longitudinal axis 19, and a canal 25 that extends generally coincident with axis 19. During primary and revision knee replacement surgery, the proximal end 18' is prepared for implantation of tibial tray component 10 by first creating a stem-receiving cavity 26 within the canal 25 in accordance with well known surgical techniques. The stem-receiving cavity 26 is defined by a stem engaging surface 84. In addition, the proximal end 18' of the tibia 18 is prepared for use with the tibial tray component 10 by forming an angled, generally planar, resected tibial surface 24. The resected surface 24 has a perimeter 23 defined by a generally "kidney" or "bean" shaped outline, although it is understood that shape of the resected surface 24 may vary in accordance with the present invention.

As used throughout the specification and claims, the terms anterior, posterior, lateral, and medial define four orthogonal directions normal to the longitudinal axis 19. Thus, anterior proximal tibia 86, posterior proximal tibia 87, lateral proximal tibia 88, and medial proximal tibia 89 are shown in FIG. 1. In order to minimize the amount of healthy bone removed during surgery, the tibial surface (not shown) is cut so that resected tibial surface 24 slopes downward, or distally, from anterior proximal tibia 86 to posterior proximal tibia 87. See FIG. 2. Thus, the amount of healthy bone preserved during surgery is maximized.

The tibial tray component 10 is also suitable for use with the femoral component 12 that is coupled to a distal femur 14. Femoral component 12 includes a femoral implant 13 coupled to the femur 14 and a bearing component 34 having a proximal, or femoral surface 45 for articulating engagement with the femoral implant 13. The bearing component 34 also includes a distal, or tibial surface 47 with spaced-apart channels 46 extending between its anterior and posterior ends for receiving a portion of the tibial tray component 10. The channels 46 themselves are defined by a bottom wall 91 and opposing side walls 92, 93 that are positioned to be at an acute and an obtuse angle relative to the bottom wall 91, respectively. See FIG. 1. While femoral component 12 is illustrated and described herein, it is understood that a wide variety of commercially available femoral components could be used with the tibial tray component 10 in accordance with the present invention.

Figure 2:
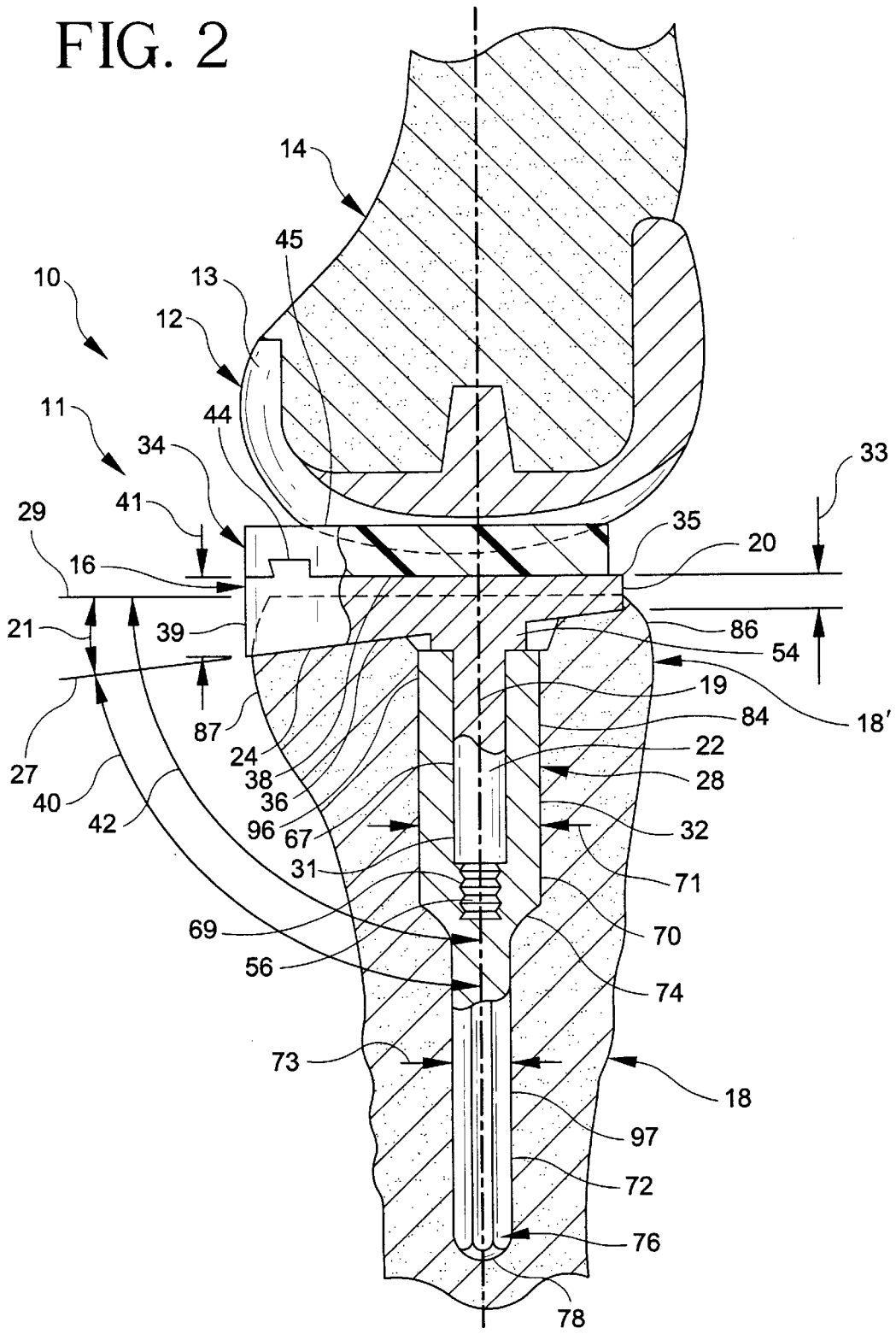
FIG. 2 is a cross-sectional view taken along line 2—2 of FIG. 1 after the prosthetic knee has been assembled showing the stem coupled to the stem extension, a dovetail coupled to the femoral component, and the plateau element having a modified wedge shape.

The tibial tray component 10 of the present invention includes a posterior-sloping plateau element 20 and a stem 22 extending from the plateau element 20. The plateau element 20 has a proximal surface 38, an opposite distal surface 36 spaced apart from the proximal surface 38, and a side wall 37 that extends between the distal and proximal surfaces 36, 38. Side wall 37 lies generally perpendicular to proximal surface 38. Illustratively, side wall 37 includes an anterior region 35 having an anterior height 33 and a posterior region 39 having a posterior height 41. Illustratively, posterior height 41 is greater than anterior height 33, giving plateau element 20 a generally posterior wedge shape. As used throughout the specification and claims the term "wedge" includes shapes with two spaced-apart and diverging surfaces. Lateral and medial side wall regions 31, 43 connect anterior region 35 to posterior region 39. As best shown in FIG. 2, the proximal surface 38 of the plateau element 20 is positioned to lie substantially parallel to a plane illustrated by line 29. Moreover, the proximal surface 38 lies substantially perpendicular to the stem 22. It is understood that in accordance with the present invention, the stem 22 may be "fixed" on the plateau element 20 to form an integral one-piece apparatus, or may be modular and coupled to the plateau element using screws, pins, rivets, adhesives, or any suitable commercially available coupling apparatus.

The distal surface 36 of plateau element 20 lies substantially in a plane illustrated by line 27 that is divergent from the plane 29 in a downward posterior direction as shown in FIG. 2. The distal surface 36 is positioned to lie at a wedge angle 21 relative to the proximal surface 38 to form a generally wedge-shaped cross-sectional shape of tibial tray component 10. The wedge angle 21 adapts the tibial tray component 10 for use with the downward posterior slope of resected surface 24 of proximal end 18' of the tibia 18. Illustratively, the wedge angle 21 is about three to about twenty degrees relative to the proximal surface 38 to conform the tibial tray component 10 for use with the resected surface 24. More preferably, the wedge angle is about three to about fifteen degrees. Most preferably, the wedge angle is about three to about ten degrees. It is understood, however, that the wedge angle 21 of the tibial tray component 10 may vary depending upon the condition of the proximal end 18' of the tibia 18.

Figure 3:
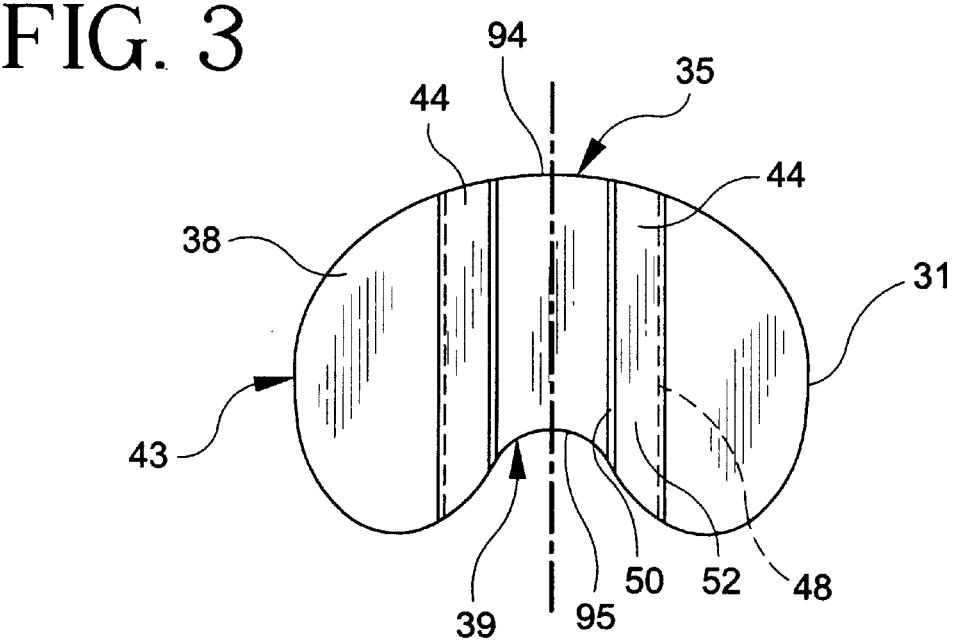
FIG. 3 is a top view of the tibial tray component of FIG. 2 showing dovetails formed on the plateau element.
Figure 4:
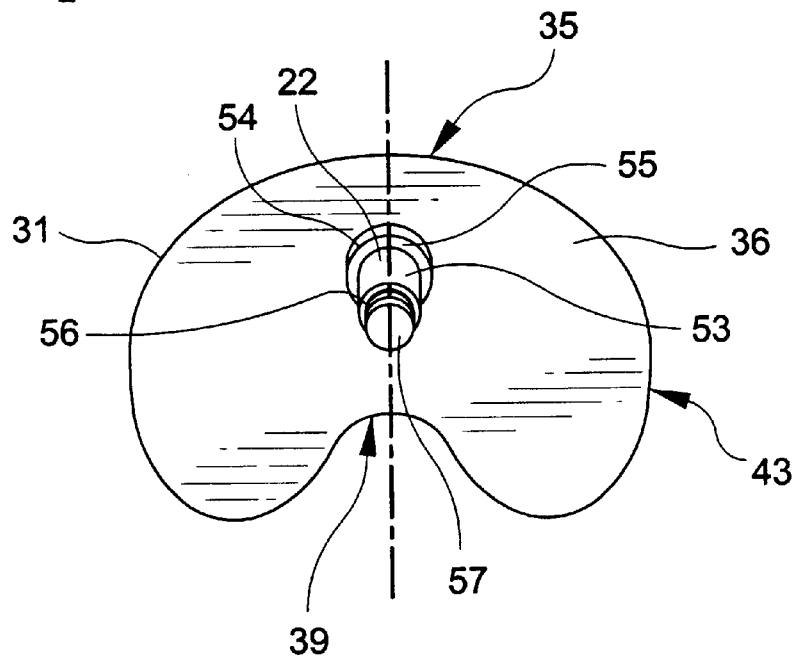
FIG. 4 is a bottom view of the tibial tray component of FIG. 2 showing the plateau element having a base and a stem extending from the base.
Figure 5:
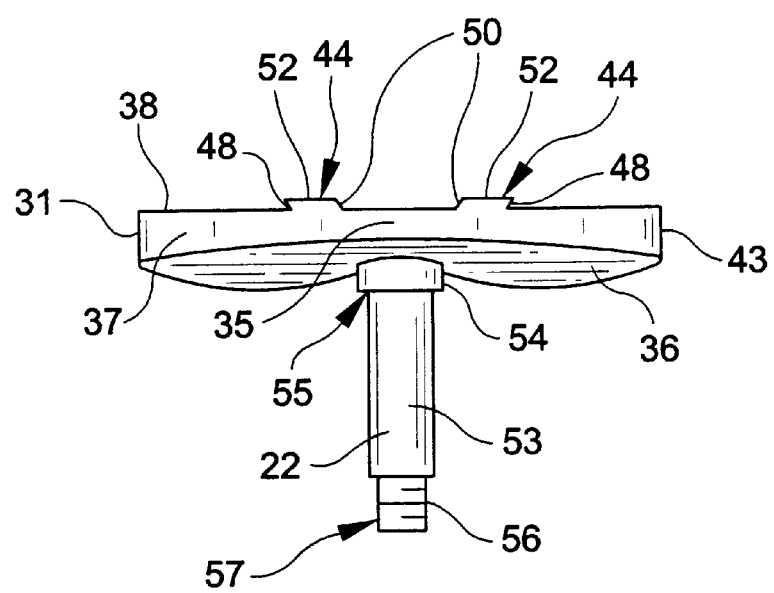
FIG. 5 is a front view of the tibial tray component of FIG. 2, showing two dovetails positioned to lie in a spaced apart relation on the plateau element.

Tibial tray component 10 also includes two dovetails 44 attached to the proximal surface 38 of the plateau element 20. Referring now to FIG. 3, the first and second dovetails 44 extend in a spaced apart and generally parallel relationship across the proximal surface 38. Illustratively, the dovetails 44 extend between the anterior and posterior sides 94, 95 of the proximal surface 38. Referring now to FIG. 5, dovetails 44 each have a top surface 52 and first and second dovetail side walls 48, 50 that extend between the proximal surface 38 of the plateau element 20 and the top surface 52. First dovetail side wall 48 defines an acute angle with respect to the proximal surface 38 and the second dovetail side wall 50 defines an obtuse angle with respect to proximal surface 38. Although two dovetails 44 are illustrated, it is understood that more or less than two dovetails may be used in accordance with the present invention. Moreover, the scope of the invention also contemplates coupling the tibial tray component 10 to the bearing component 34 of the femoral component 12 using screws, pins, adhesives or the like. In addition, it is within the scope of the present invention to mold the bearing component 34 on the component 10. Further, proximal surface 38 may be formed with spaced apart channels (not shown) thereon, while the bearing component 34 is formed with cooperating dovetails (not shown). The dovetails could also extend in a lateral-medial direction instead of the anterior-posterior direction of the illustrated embodiment.

The stem 22 of the tibial tray component 10 includes a stem base region 54 extending from the distal surface 36 of the plateau element 20, distal threads 56, and a generally cylindrical stem shaft 53. As shown in FIG. 5, the stem shaft 53 extends between the base region 54 and the distal threads 56. Moreover, stem 22 includes an annular base lip 55. The stem shaft 53 extends from the stem base region 54 adjacent the base lip 55. It is understood that the stem 22 may be formed in any number of shapes and sizes in accordance with the present invention. In addition, the stem 22 may include a porous coating and be formed to couple directly with the tibia 18.

In preferred embodiments, the tibial tray component 10 is suitable for use with the tibial stem extension 28. The tibial stem extension 28 includes a cylindrical upper portion 70 and a lower portion 72. The shape and dimensions of the stem extension 28 may be varied to provide for adapting the stem 22 of tibial tray component 10 to a range of shapes and sizes of stem-receiving cavities 26 in the proximal end 18' of the tibia 18 without affecting the relative dimensions of tibial tray component 10. The upper portion 70 of stem extension 28 further includes an opening 66 to an interior cylindrical wall 67. The cylindrical wall 67 defines a stem-receiving cavity 30 within stem extension 28. The stem-receiving cavity 30 is sized to receive the stem 22 of the tibial tray 10 therein. In addition, the interior cylindrical wall 67 includes a threaded region 69 for engaging distal threads 56 on stem 22. The interior cylindrical wall 67 further includes an annular bevel 68 adjacent opening 66 into the cavity 30 and to facilitate entry of stem 22 into the stem-receiving cavity 30.

Tibial stem extension 28 has a longitudinal axis 75 extending therethrough. Upper portion 70 of stem extension 28 is substantially coaxial with longitudinal axis 75 and has an annular rim surface 62 that lies substantially perpendicular to longitudinal axis 75. The rim 62 extends between the annular bevel 68 and an outer wall 96 of upper portion 70 of stem extension 28. The stem base region 54 of stem 22 abuts annular rim surface 62 as shown in FIG. 2 when the stem 22 of tibial tray component 10 is fully assembled with stem extension 28. Lower portion 72 of stem extension 28 includes an outer wall 97 and is also generally coaxial with longitudinal axis 75. The diameter of the lower portion 72 is smaller than the diameter of the upper portion 70. The illustrated lower portion 72 is further formed with six longitudinal flutes 76 extending substantially the length of lower portion 72 and terminating adjacent a rounded tip 78 at distal end 60 of stem extension 28. It is understood, however, that the lower portion 72 may also be formed without flutes 76. A transition region 74 is positioned to lie between the lower portion 72 and the upper portion 70.

Although the stem 22 and stem extension 28 have been described with reference to particular embodiment, the scope of the invention contemplates any stem or stem extension that provides for coupling the one-piece tibial tray component 10 to the proximal end 18' of tibia 18. In addition, any suitable geometry for coupling the stem 22 to the stem extension 28 is acceptable, e.g., a stem having a tapered shape that couples with a stem extension by means of a friction fit or the like (not shown). Similarly, in place of the stem extension 28 having upper and lower portions 70, 72 with flutes 76 on the lower portion 72 as shown in FIGS. 1 and 2, the invention contemplates a stem extension of arbitrary geometry for coupling with the stem engaging surface 84, e.g., a tapered stem extension or a stem extension sized smaller than the stem-receiving cavity 26 and coupled to stem engaging surface 84 with bone cement (not shown). Moreover, the present invention contemplates the stem 22 being formed for extension directly into the stem-receiving cavity 26 of proximal tibia 18 and engagement with the stem engaging surface 84.

Tibial tray component 10 according to the present invention is assembled into a prosthetic knee 11 in the following manner. The femoral implant 13 of the femoral component 12 is coupled to distal femur 14 in accordance with well known surgical techniques. The resected surface 24 and stem-receiving cavity 26 of proximal end 18' of tibia 18 are also prepared as previously discussed. As shown in FIG. 2, the posterior slope of the resected surface 24 is defined by the difference between stem plateau angle 42 and stem base angle 40. The posterior slope is about three to about twenty degrees in a distal direction, more preferably about three to about fifteen degrees, and most preferably about three to about ten degrees.

Tibial tray component 10 is coupled to stem extension 28 by inserting the stem shaft 53 of the stem 22 past the annular bevel 68 and into stem-receiving cavity 30. Once inserted, the stem extension 28 is rotated on the stem shaft 53 until the distal threads 56 on the stem 22 are coupled to the threaded region 69 of the interior cylindrical wall 67. In preferred embodiments, the base lip 55 of the stem 22 rests upon the annular rim 62 of the stem extension 28 when the threads 56 are coupled to the threaded region 69 and the stem 22 is fixed on the stem extension 28.

The lower portion 72 of the stem extension 28 is then inserted into stem-receiving cavity 26 until the distal surface 36 of plateau element 20 lies adjacent resected surface 24 as shown in FIG. 2. For purposes of secure mounting, bone cement (not shown) is provided between the distal surface 36 of plateau element 20 and the resected surface 24. As shown in FIG. 2, in the inserted position the stem 22 of tibial tray component 10 is positioned to lie generally parallel to longitudinal axis 19 and the proximal surface 38 is positioned to lie generally perpendicular to longitudinal axis 19. In addition, the tibial tray component 10 is oriented on the resected surface 24 such that the anterior region 35 lies above the anterior proximal tibia 86 and the posterior region 39 lies above the posterior proximal tibia 87.

To complete assembly of the prosthetic knee 11, the bearing component 34 of the femoral component 12 is coupled to tibial tray component 10. First the dovetails 44 are aligned with the channels 46 formed in the bearing component 34 in a side-by-side relationship. Once aligned, the side walls 48, 50 of the dovetails 44 are slid into the channels 46. The dovetails 44 are held within the channels 46 by the frictional engagement of the side walls 48, 50 of the dovetails 44 and the side walls 92, 93 of the channels 46. See FIGS. 1 and 2. Once the tibial tray component 10 has been coupled to the bearing component 34, the bearing component 34 is coupled to the femoral implant 13 using well known surgical techniques.

Figure 6:
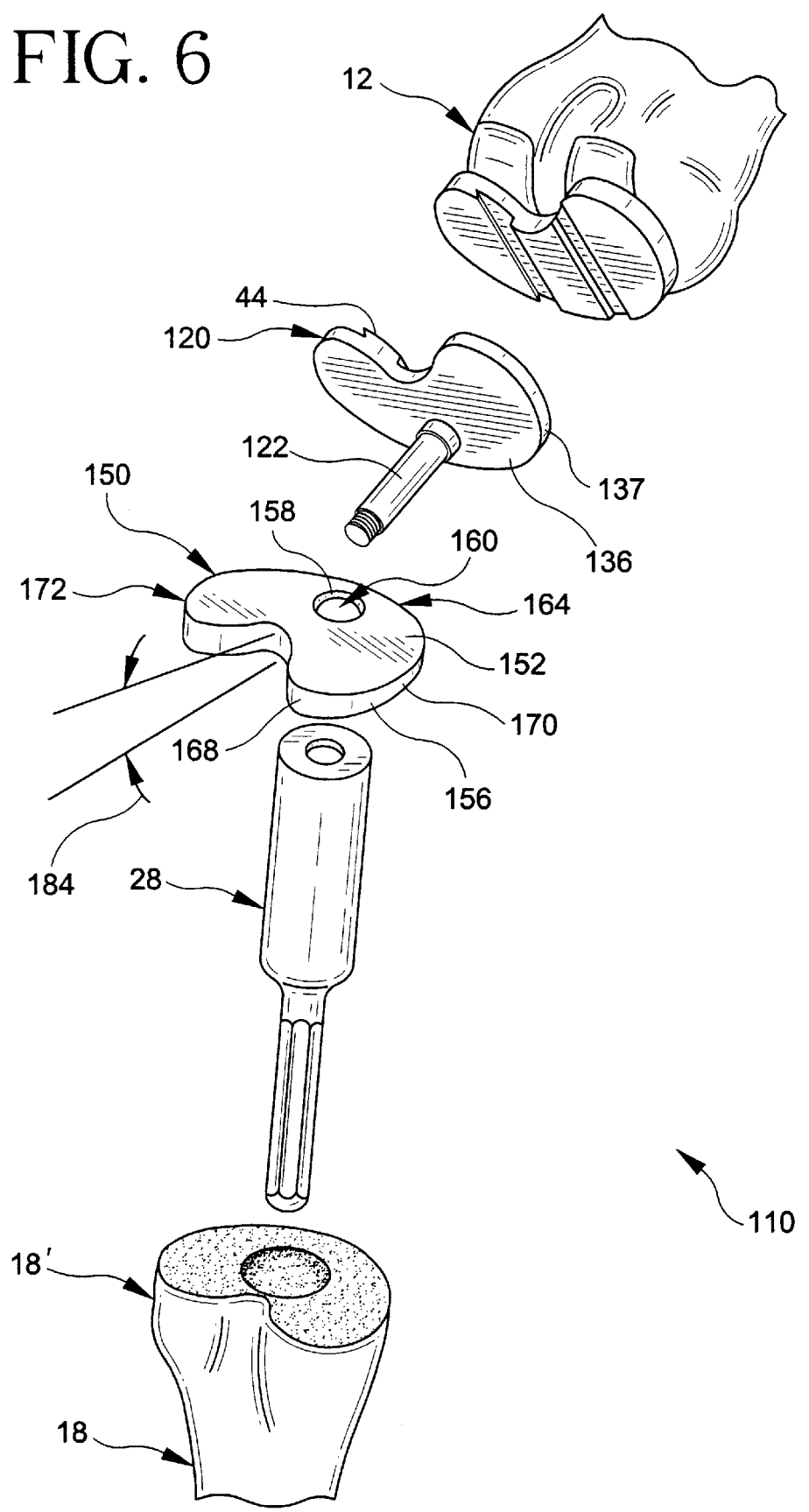
FIG. 6 is a view similar to FIG. 1 of another alternative embodiment of a tibial tray apparatus of the present invention showing a posterior-sloping generally wedge-shaped posterior compensation element including an aperture therethrough and a tibial tray including a plateau element having a stem.

In an alternative embodiment of the present invention, a tibial tray component 110 includes a plateau element 120 and a wedge-shaped posterior compensation element 150. See FIGS. 6 and 7. The plateau element 120 has a proximal surface 138, an opposite distal surface 136 spaced apart from the proximal surface 138, and a side wall 137 that extends between the distal and proximal surfaces 136, 138. A stem 122 extends from the distal surface 136 of the plateau element 120. It is understood that the stem 122 may be formed integrally with the plateau element 120, or may be mounted on the plateau element 120 using threads, screws, pins, or the like. Moreover, the proximal surface 138 plateau element 120 is positioned to lie in a generally parallel relationship with the distal surface 136. It is understood, however, that the distal surface 136 may diverge from the proximal surface 138.

The wedge element 130 has a proximal surface 152, an opposite distal surface 154 spaced apart from the proximal surface 152, a side wall 156 that extends between the proximal and distal surfaces 152, 154, and an edge 158 defining an aperture 160. Proximal surface 152 of wedge-shaped posterior compensation element 150 is configured to couple to distal surface 136 of plateau element 120. In the illustrated embodiment, proximal surface 152 of wedge element 130 is coupled to distal surface 136 of plateau element 120 by means of an adhesive such as glue or cement (not shown). It is understood, however, that the surfaces 136, 152 can be coupled by any suitable mechanism, such as screws, bolts, pins, or any suitable attachment mechanism.

The aperture 160 in wedge-shaped posterior compensation element 150 is sized to receive the stem 122 therethrough. See FIG. 7. Moreover, the side wall 156 of wedge-shaped posterior compensation element 150 lies generally perpendicular to proximal surface 152 and includes an anterior region 162 having an anterior height 164 and a posterior region 166 having a posterior height 168. Posterior height 168 is greater than anterior height 164 to give posterior compensation element 150 its general wedge shape. Lateral and medial side wall regions 170, 172 connect anterior region 166 to posterior region 178.

Figure 7:
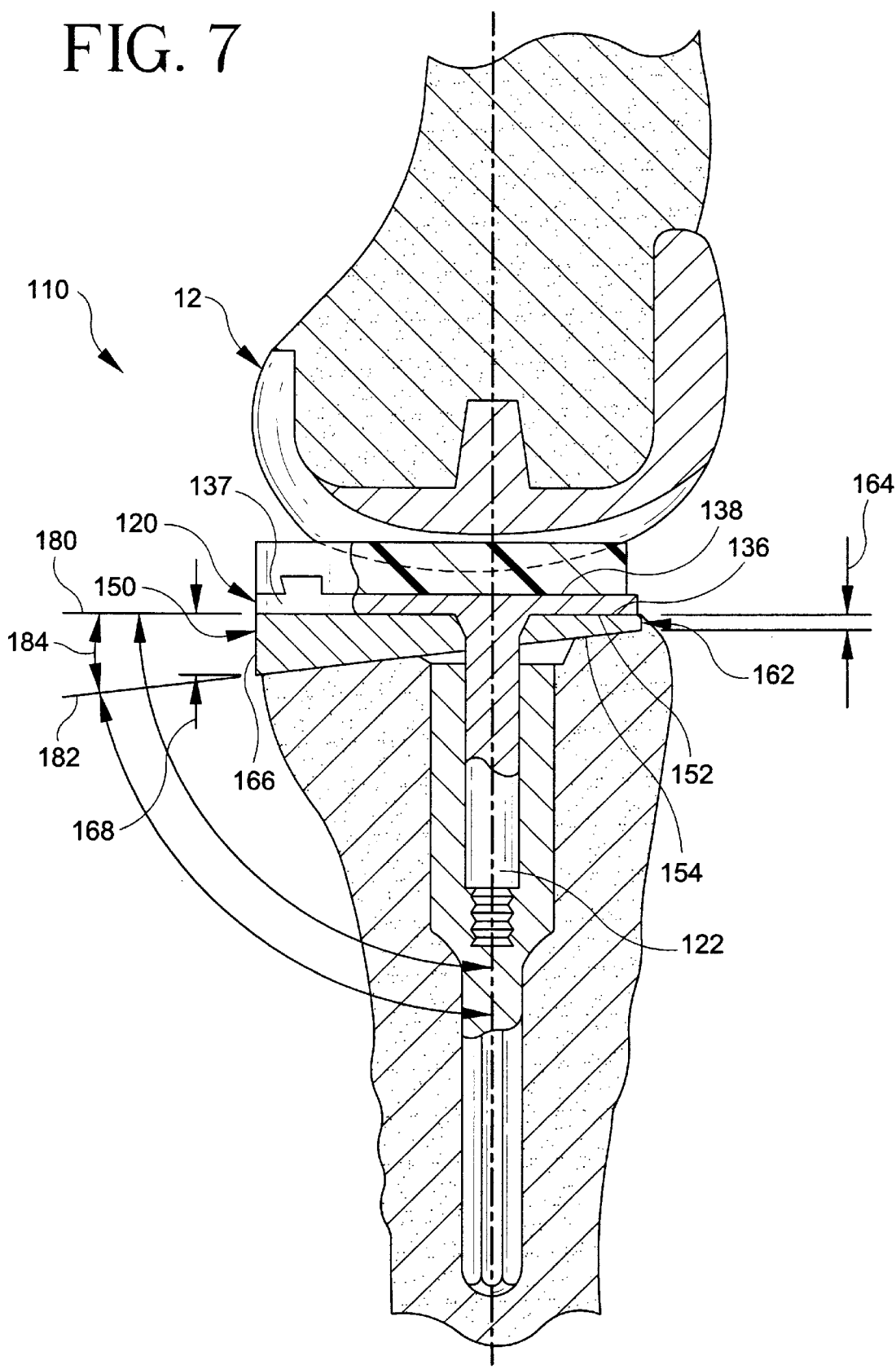
FIG. 7 is a view similar to FIG. 2 of the tibial tray apparatus of FIG. 6, showing the generally wedge-shaped posterior compensation element including a distal surface engaging a resected surface of the tibia and a proximal surface engaging a distal surface of the tibial tray and showing the stem of the tibial tray extending through the aperture formed in the modular component.

The proximal surface 152 of wedge-shaped posterior compensation element 150 lies substantially in a plane illustrated by line 180 and the distal surface 154 lies substantially in a plane illustrated by line 182 that diverges from the plane 180 in a downward posterior direction by a wedge angle 184 as shown in FIG. 7. Illustratively, the wedge angle 184 can be from about three degrees to about twenty degrees, although the invention contemplates any wedge angle that adapts the posterior compensation element 150 for use with the proximal end 18' of the tibia 18 that is resected with a downward posterior slope. Moreover, it is understood that the wedge-shaped posterior compensation element 150 may cooperate with the plateau element 120 having a general wedge shape to define a wedge angle between the proximal surface 138 of plateau element 120 and the distal surface 154 of the posterior compensation element of about three to about twenty degrees.

The plateau element 120 further includes two dovetails 44 attached to the proximal surface 138 as discussed above. As previously discussed, the scope of the invention contemplates replacing dovetails 44 with any suitable configuration that couples the tibial tray component 110 to the bearing component 34 of the femoral component 12. The stem 122 of plateau element 120 is similarly configured as the stem 22 extending from the generally wedge-shaped tibial tray component 10 discussed above.

Figure 2A:
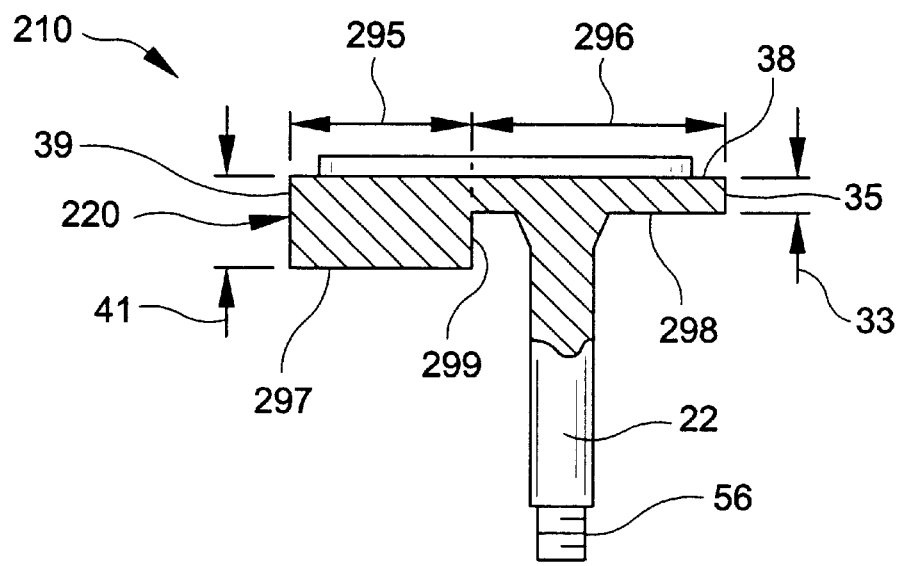
FIG. 2a is a view similar to FIG. 2, showing a cross-sectional view of an alternative embodiment of the present invention having a block wedge or stepped plateau element and a stem coupled to a distal surface of the plateau element.

In another alternative embodiment of the present invention, a tibial tray component 210 includes a block wedge or stepped plateau element 220. See FIG. 2a. Features of tibial tray component 210 that are the same as features in tibial tray component 10 in FIG. 2 are indicated by the same reference numerals in FIG. 2a. Stepped plateau element 210 includes a posterior distal surface 297 and an anterior distal surface 298. Posterior distal surface 297 is spaced apart from proximal surface 38 by the posterior height 41 adjacent posterior region 39 and anterior distal surface is spaced apart from proximal surface 38 by the anterior height 33 adjacent anterior region 35. Posterior distal surface 297 is connected to anterior distal surface 298 by a transition region 299. Posterior distal surface 297 extends a first distance 295 from posterior region 39 to transition region 299 and anterior distal surface extends a second distance 296 from anterior region 35 to transition region 299. It is understood that the location of the transition region 299 can vary in the anterior-posterior direction, that is, first and second distances 295, 296 can vary. It is understood that posterior and anterior distal surfaces 297, 298 can be generally parallel to proximal surface 38 or may diverge in a downward posterior direction. Furthermore, transition region 299 can be generally perpendicular to proximal surface 38 or may have a downward posterior slope. Stepped plateau element 220 further includes a stem 22 extending from anterior distal surface 298. It is understood, however, that stem 22 can extend from posterior distal surface 297 or from the transition region 299 if the transition region 299 is sloped. When using the tibial tray component 210, the proximal end 18' of the tibia 18 is resected with a surface (not shown) that corresponds to the stepped configuration of the distal surfaces 297, 298, 299 of the block wedge or stepped plateau element 220.

Figure 7A:
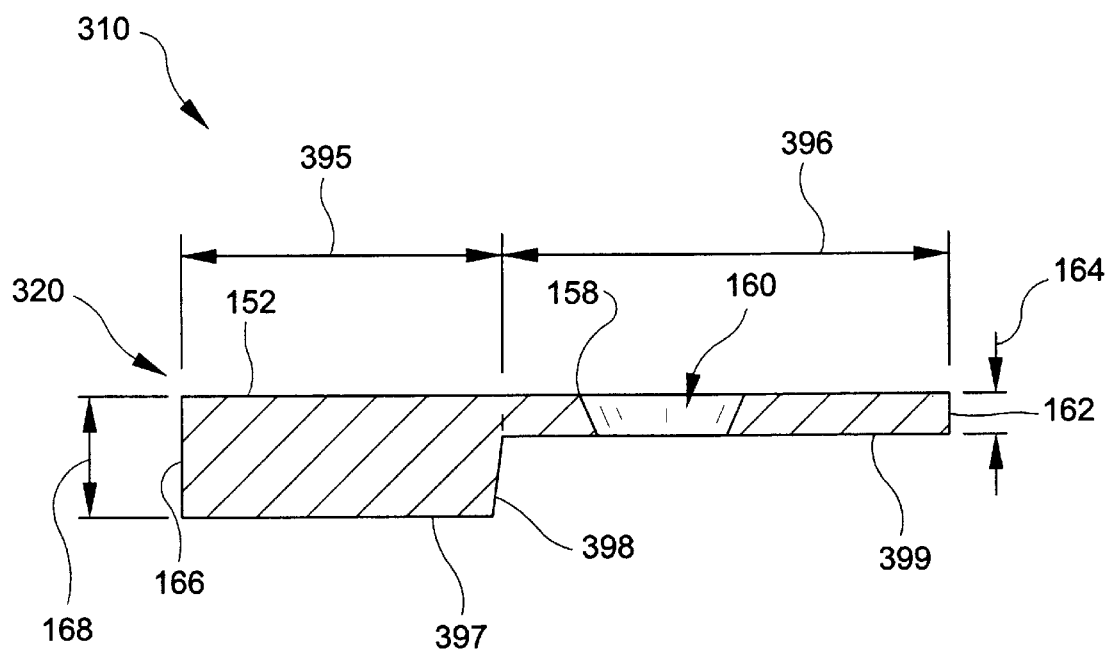
FIG. 7a is a view similar to FIG. 7, showing a cross-sectional view of yet another alternative embodiment of the present invention having a block wedge or stepped posterior compensation element having an aperture therethrough.

In yet another alternative embodiment according to the present invention, a tibial tray component 310 includes a block wedge or stepped plateau element 320. See FIG. 7a. Features of tibial tray component 310 that are the same as features in tibial tray component 110 in FIG. 7 are indicated by the same reference numerals in FIG. 7a. Stepped plateau element 310 includes a posterior distal surface 397 and an anterior distal surface 398. Posterior distal surface 397 is spaced apart from proximal surface 152 by the posterior height 168 adjacent posterior region 166 and anterior distal surface 398 is spaced apart from proximal surface 152 by the anterior height 164 adjacent anterior region 162. Posterior distal surface 397 is connected to anterior distal surface 398 by a transition region 399. Posterior distal surface 397 extends a first distance 395 from posterior region 166 to transition region 399 and anterior distal surface extends a second distance 396 30 from anterior region 162 to transition region 399. It is understood that the location of the transition region 399 can vary in the anterior-posterior direction, that is, first and second distances 395, 396 can vary. It is understood that posterior and anterior distal surfaces 397, 398 can be generally parallel to proximal surface 152 or may diverge in a downward posterior direction. Furthermore, transition region 399 can be generally perpendicular to proximal surface 152 or may have a downward posterior slope. Stepped plateau element 320 further includes an edge 158 defining an aperture 160 that extends between proximal surface 152 and anterior distal surface 399. It is understood, however, that aperture 160 can extend between proximal surface 152 and posterior distal surface 397 or between proximal surface 152 and transition region 399 if transition region 399 is sloped. When using the tibial tray component 310, the proximal end 18' of the tibia 18 is resected with a surface (not shown) that corresponds to the stepped configuration of the distal surfaces 397, 398, 399 of the block wedge or stepped plateau element 320.

The tibial tray component of the present invention provides users with a prosthetic component that is useful in both primary and revision knee replacement. Moreover, the tibial tray component 10 is useful for preserving good bone.

Although the invention has been described in detail with reference to certain preferred embodiments, variations and modifications exist within the scope and spirit of the invention as described and defined in the following claims.

What is claimed is:

1. A tibial tray apparatus suitable for replacing at least a portion of a proximal tibia having an anterior end, a posterior end, and a resected surface extending between the anterior and posterior ends, the tibia tray apparatus comprising:

a posterior compensation element including a proximal surface lying in a first plane, an opposite distal surface configured for extension across the resected surface between the anterior and posterior ends, and a side wall extending between the proximal and distal surfaces, the side wall including an anterior region having an anterior height and a posterior region having a posterior height, the posterior height being greater than the anterior height;

a stem being unitary with and extending from the distal surface generally perpendicular to the first plane; and a stem extension including an interior surface defining a stem-receiving cavity therein and the stem is sized for extension into the stem-receiving cavity.

2. A tibial tray apparatus suitable for replacing at least a portion of the proximal end of a tibia and for cooperation with a femoral component, the tibial tray apparatus comprising:

a plateau element including a proximal surface lying in a first plane, an opposite distal surface, and a side wall extending between the proximal and distal surfaces, the side wall having an anterior region perpendicular to the proximal surface and at an acute angle to the distal surface and a posterior region perpendicular to the proximal surface and at an obtuse angle to the distal surface, and a stem connected to and being unitary with the distal surface of the plateau element.

3. The apparatus of claim 2, wherein the stem is positioned to lie along an axis and the proximal surface lies in a plane generally perpendicular to the axis.

4. The apparatus of claim 2, wherein the side wall includes opposite side regions that extend between the posterior and anterior regions, and each of the side regions converges from the posterior region toward the anterior region of the side wall.

5. The apparatus of claim 2, wherein the distal surface is positioned to lie in a plane at an angle of about 3 to about 20 degrees relative to the proximal surface.

6. The apparatus of claim 2, wherein the plateau element is formed to include an attachment mechanism configured to couple a bearing component thereto.

7. The apparatus of claim 6, wherein the attachment mechanism comprises at least one dovetail.

8. The apparatus of claim 7, wherein the at least one dovetail extends across the proximal surface between the anterior and posterior regions.

9. A tibial tray apparatus suitable for replacing at least a portion of the proximal end of a tibia and for cooperation with a femoral component, the tibial tray apparatus comprising:

a plateau element including a proximal surface, an opposite distal surface, and a side wall extending between the proximal and distal surfaces, the side wall having an anterior region having an anterior height and an opposite posterior region having a posterior height, the posterior height being greater than the anterior height, and a stem integral with and extending from the distal surface of the plateau element, the plateau element being formed to include an attachment mechanism configured to couple a bearing component thereto, the attachment mechanism comprising at least one dovetail, and the at least one dovetail including a first side wall positioned to lie at an obtuse angle relative to the proximal surface, a second side wall positioned to lie at an acute angle relative to the proximal surface, and a top surface extending between the first and second side walls.

10. A tibia tray apparatus suitable for replacing at least a portion of the proximal end of a tibia and for cooperation with a femoral component, the tibial tray apparatus comprising:

a plateau element including a proximal surface, an opposite distal surface, and a side wall extending between the proximal and distal surfaces, the side wall having an anterior region having an anterior height and an opposite posterior region having a posterior height, the posterior height being greater than the anterior height, and a stem integral with and extending from the distal surface of the plateau element, the plateau element being formed to include an attachment mechanism configured to couple a bearing component thereto, and the attachment mechanism comprises two dovetails, each having a first side wall disposed at an acute angle to the proximal surface and a second side wall disposed at an obtuse angle to the proximal surface.

11. A prosthetic apparatus suitable for replacing at least a portion of a tibia and for cooperation with a femoral component, the prosthetic apparatus comprising:

a one-piece tibial tray including a plateau and a stem, the plateau having a proximal surface lying in a first plane and a distal surface cooperating to define an anterior region with an anterior height and an opposite posterior region with a posterior height that is greater than the anterior height, and the stem extending from the distal surface generally perpendicular to the first plane; and a stem extension including an interior surface defining a stem-receiving cavity therein, the interior surface being configured for locking engagement with the stem of the tibial tray component.

12. The apparatus of claim 11, wherein the distal surface is positioned to lie in a plane at an angle of about 3 to about 20 degrees relative to the first plane.

13. The apparatus of claim 11, wherein the plateau includes a side wall extending between the proximal and distal surfaces and the side wall includes opposite side regions that extend between the posterior and anterior regions, and each of the side regions converges from the posterior region toward the anterior region.

14. A prosthetic apparatus suitable for replacing at least a portion of a tibia and for cooperation with a femoral component, the prosthetic apparatus comprising:

a tibial tray including a plateau having a proximal surface lying in a first plane and a distal surface cooperating to define an anterior region with an anterior height and an opposite posterior region with a posterior height that is greater than the anterior height, and a stem extending from the distal surface generally perpendicular to the first plane; and a stem extension including an interior surface defining a stem-receiving cavity therein, the interior surface being configured for locking engagement with the stem of the tibial tray component, the plateau including dovetails positioned to lie in a spaced apart generally parallel relationship.

15. The apparatus of claim 14, wherein the dovetails include a first side wall positioned to lie at an obtuse angle relative to the proximal surface, a second side wall positioned to lie at an acute angle relative to the proximal surface, and a top surface extending between the first and second side walls.

16. A method of replacing a proximal end of a tibia that includes a posterior end and an opposite anterior end, the method comprising the steps of:

forming a resected surface of the proximal tibia to have a distal posterior slope, creating a stem-receiving cavity in the proximal tibia, providing a generally wedge-shaped plateau component having a proximal surface, an opposite distal surface, and a stem extending from and integral with the distal surface, the distal surface diverging from the proximal surface by a downward posterior wedge angle to form an anterior region with an anterior height and a posterior region with a posterior height that is greater than the anterior height, and positioning the distal surface of the generally wedge-shaped plateau component on the resected surface so that posterior region of the generally wedge-shaped plateau component is adjacent the posterior end and the stem is received in the stem-receiving cavity.

17. The method of claim 16, wherein the wedge angle is about three degrees to about twenty degrees.

18. The method of claim 17, wherein the wedge angle is about three to about fifteen degrees.

19. The method of claim 17, wherein the wedge angle is about three to about ten degrees.

20. The method of claim 16, further comprising the step of providing a stem extension configured to couple with the proximal tibia and the stem, and wherein the positioning step further comprises the steps of coupling the stem extension with the stem and inserting the stem extension into the stem-receiving cavity.

21. The method of claim 20, further comprising the step of applying cement between the proximal tibia and the wedge-shaped plateau component.

22. The method of claim 16, further comprising a tibial tray having a tray plateau element and further comprising the step of coupling the tibial tray and the generally wedge-shaped plateau component together.

23. The method of claim 22, wherein the tray plateau element includes a proximal surface and a generally parallel distal surface and the proximal surface of the generally wedge-shaped plateau component is coupled to the distal surface of the tray plateau element.

24. The method of claim 23, wherein the step of coupling the proximal surface of the generally wedge-shaped plateau component to the distal surface tray plateau element comprises applying cement between the two surfaces.

\* \* \* \* \*